US00PP11971P2

(12) United States Plant Patent
Heffner

(10) Patent No.: US PP11,971 P2
(45) Date of Patent: Jul. 3, 2001

(54) VARIETY OF PETUNIA NAMED 'TRUMPET PURPLE'

(75) Inventor: Mike Heffner, Lompoc, CA (US)

(73) Assignee: John Bodger and Sons Company, South El Monte, CA (US)

( * ) Notice: Subject to any disclaimer, the term of this patent is extended or adjusted under 35 U.S.C. 154(b) by 0 days.

(21) Appl. No.: 09/169,797

(22) Filed: Oct. 9, 1998

(51) Int. Cl.[7] ..... A01H 5/00

(52) U.S. Cl. ..... Plt./356

(58) Field of Search ..... Plt./356

(56) References Cited

U.S. PATENT DOCUMENTS

P.P. 6,915 * 7/1989 Tsuda et al. ..... Plt./356
P.P. 10,028 * 9/1997 Rother ..... Plt./356

* cited by examiner

*Primary Examiner*—Bruce R. Campell
*Assistant Examiner*—Wendy C. Baker
(74) *Attorney, Agent, or Firm*—Fulwider Patton Lee & Utecht, LLP

(57) ABSTRACT

The claimed cultivar brings a new color to the Trumpet series of Petunias and is characterized by a purple colored flower accented in its center with dark purple veining, over medium green foliage. As with all Trumpet Petunias, this cultivar exhibits early flowering with superior branching so that the plant may also be used in a hanging pot.

1 Drawing Sheet

BACKGROUND OF THE NEW PLANT

The present invention relates to a new and distinct variety of Petunia known by the name 'Trumpet Purple' (Bodger No. 7P3415-3). The new variety was discovered in a selective breeding program by Mike Heffner at Bodger Seeds, Ltd., Lompoc, Calif. The new variety is a selection from the crossing of inventor's proprietary Petunia selection Bodger No. 7P697-1 (unpatented) which is a seedling with vigorous spreading habit and small burgundy colored flowers, with inventor's proprietary Petunia selection Bodger No. 7P1107-2 (unpatented) which is a seedling with upright habit and large salmon colored flowers.

This new variety is the result of a breeding program whose objective was to develop new vegetatively propagated petunias with a spreading cascading habit, large flowers and with a color range not presently available as a cutting product. The variety originated from a cross between two proprietary seedling selections taken from the existing breeding program. The progeny from this cross was grown out during the summer of 1997 and a number of single plants were selected as possible new varieties and propagated vegetatively. The cuttings were trialed and evaluated during winter and summer of 1998 at which time it was determined that this particular line, established from one single plant, was distinguishable and unique.

The new cultivar was first asexually reproduced by terminal vegetative cuttings at Bodger Seeds, Ltd., Lompoc, Calif. and has been repeatedly asexually reproduced by cuttings at Bodger Seeds Ltd., at Lompoc Calif. It has been found to be stable and true to type through successive propagations.

The new cultivar, was grown in a glass greenhouse in Lompoc, Calif., using full light, 60° Fahrenheit night temperature, 77° Fahrenheit day temperature, and grown in soil having a temperature of 80° Fahrenheit. The claimed plant was grown from a terminal vegetative cutting, and exhibited an eight to ten weeks response time from an unrooted cutting to a 25 cm flowering plant.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Bodger Seeds Ltd., in Lompoc, Calif. The plant histories were taken on rooted cuttings believed to have been potted in a 25 cm pot, under full light in the greenhouse, and color readings were taken in day light using The Royal Horticultural Society of London Colour Chart.

THE PLANT

Classification:
- *Botanical.*—*Petunia×hybrida Hort.*
- *Commercial.*—Petunia named 'Trumpet Purple'.

Form: Indeterminate, freely branching, with spreading and decumbent habit. When planted in a hanging pot the stems hang down.
- *Height.*—17.5 cm above the top of pot.
- *Spreading area of plant.*—96 cm in diameter.

Leaves: Leaves are simple, opposite at base and tip of stem, alternate in center; pinnate venation; foliage viscid; leaves horizontal to stem.
- *Size.*—6.7 cm length when fully expanded. 3.6 cm width when fully expanded. 1.0 mm thickness.
- *Shape.*—Elliptic.
- *Margin.*—Entire.
- *Texture.*—Sparsely pubescent.
- *Color.*—Adaxial: Green Group 137C. Abaxial: Yellow-Green Group 144A.
- *Apex.*—Broadly acute.
- *Base*—Attenuate.

Stem:
- *General.*—Hanging; Spreading to a length of 48 cm.

*Color.*—Green Group 143B.
*Internode length.*—3.6 cm.
*Diameter.*—0.4 cm.
*Anthocyanin pigmentation.*—Absent.
*Texture.*—Pubescent.

INFLORESCENCE

Young flower:
*Diameter.*—5.7 cm.
*Length.*—4.4 cm.
*Color.*—Adaxial: Red-Purple Group 71A, with dark Purple Group 79B at the veins in the center. Abaxial: Purple-Violet Group 80B with veins in Yellow-Green Group 152B, outer edge is Purple-Violet Group 80D with base Purple Group 75D.

Mature flower:
*Diameter.*—7.9 cm.
*Length.*—6.3 cm.
*Color.*—Adaxial: Red-Purple Group 74A, with dark Purple Group 79B at the veins in the center. Abaxial: Purple-Violet Group 80B with veins in Yellow-Green Group 152B, outer edge is Purple-Violet Group 80D with base Purple Group 75D.

Open florets:
*Form.*—Single funnelform flowers; calyx five parted, petals united into flower tube; petal apex broadly acuminate to rounded.
*Texture and appearance.*—Smooth on adaxial, pubescent on abaxial, presenting large purple flowers.

Pedicel:
*Length.*—3.3 cm.
*Thickness.*—0.2 cm.
*Texture.*—Pubescent.

Sepals:
*Quantity.*—5.
*Length.*—2.8 cm.
*Width.*—1.0 cm.
*Shape.*—Elliptic.
*Color.*—Adaxial Yellow-Green Group 147A. Abaxial Yellow-Green Group 147B.
*Apex.*—Obtuse.
*Margin.*—Entire.
*Texture.*—Pubescent.

Persistence:
*Disease resistance.*—Not known.

REPRODUCTIVE ORGANS

Stamens:
*Number.*—5 normal stamens.
*Anthers.*—3 level with stigma; 2, 6 mm above stigma; Blue.
*Filaments.*—Green-White.

Pistils:
*Number.*—1 normal.
*Stigma.*—Green.
*Style.*—Yellow-Green.

Ovaries: Superior.

GENERAL CHARACTERISTICS

'Trumpet Purple' brings a new and distinct color to the Trumpet Series of Petunias which is a group of varieties that are early flowering and very floriferous having large blooms over a medium green foliage. At maturity 'Trumpet Purple' has approximately 100–150 open blooms per 25 cm pot. 'Trumpet Purple' presents a large purple colored flower accented with darker purple veins in its center. The flowers open above the foliage facing outwards and have no fragrance. The lastingness of individual blooms is the approximately two weeks, the same as seed grown petunias. The variety shows normal fertility and seed set.

I claim:

1. A new and distinct variety of Petunia plant, substantially as shown and described.

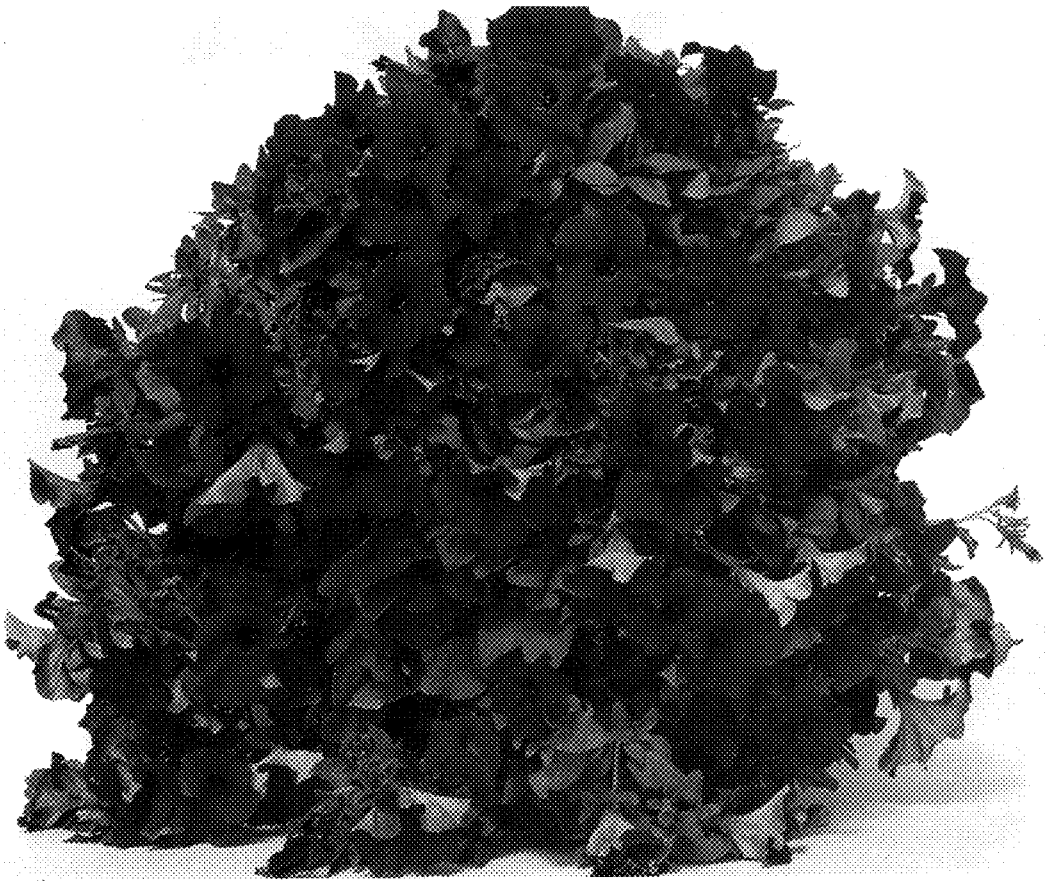

* * * * *